United States Patent [19]

Robert

[11] Patent Number: 5,695,338
[45] Date of Patent: Dec. 9, 1997

[54] EXPANSION DEVICE FOR ORAL RECONSTRUCTION AND METHOD FOR THE INSTALLATION OF THE EXPANSION DEVICE UNDER A PATIENT'S GUM IN ORDER TO CARRY OUT ORAL RECONSTRUCTION IN CASES OF BONE LOSS

[76] Inventor: Antoine Robert, c/o Mr. and Mme Lottmann 106, avenue Félix Faure, 75015 Paris, France

[21] Appl. No.: 403,805

[22] PCT Filed: Sep. 15, 1993

[86] PCT No.: PCT/FR93/00890

§ 371 Date: May 15, 1995

§ 102(e) Date: May 15, 1995

[87] PCT Pub. No.: WO94/06368

PCT Pub. Date: Mar. 31, 1994

[30] Foreign Application Priority Data

Sep. 15, 1992 [FR] France ................... 92 10992

[51] Int. Cl.[6] .................................................. A61C 5/00
[52] U.S. Cl. ......................... 433/215; 433/175; 623/8
[58] Field of Search .......................... 433/215, 229, 433/175; 623/7, 8, 10, 11

[56] References Cited

U.S. PATENT DOCUMENTS

| | | | |
|---|---|---|---|
| 3,343,263 | 9/1967 | Henlotter | 32/10 |
| 4,671,255 | 6/1987 | Dubrul et al. | 128/1 R |
| 4,719,918 | 1/1988 | Bonomo et al. | 128/344 |
| 4,908,029 | 3/1990 | Bark et al. | 623/8 |
| 5,066,303 | 11/1991 | Bark et al. | 623/8 |
| 5,074,878 | 12/1991 | Bark et al. | 623/8 |
| 5,083,576 | 1/1992 | Ruiz-Razura et al. | 623/8 |
| 5,104,409 | 4/1992 | Baker | 623/8 |
| 5,137,529 | 8/1992 | Watson et al. | 604/891.1 |
| 5,358,521 | 10/1994 | Shane | 623/8 |
| 5,480,430 | 1/1996 | Carlisle et al. | 623/8 |

FOREIGN PATENT DOCUMENTS

| | | |
|---|---|---|
| 0196821 | 10/1986 | European Pat. Off. . |
| 0260081 | 3/1988 | European Pat. Off. . |
| 2608916 | 7/1988 | France . |

*Primary Examiner*—Nicholas D. Lucchesi
*Attorney, Agent, or Firm*—Nilles & Nilles

[57] ABSTRACT

An expansion device for oral reconstruction formed by a closed pouch made of a film provided at one point with an additional thickness and a protective feature against being perforated right through, characterized in that the protective feature is a concave cover portion within the pouch and is positioned so as to be facing the additional thickness, bonded directly to each side of the additional thickness but not on its entire periphery.

18 Claims, 5 Drawing Sheets

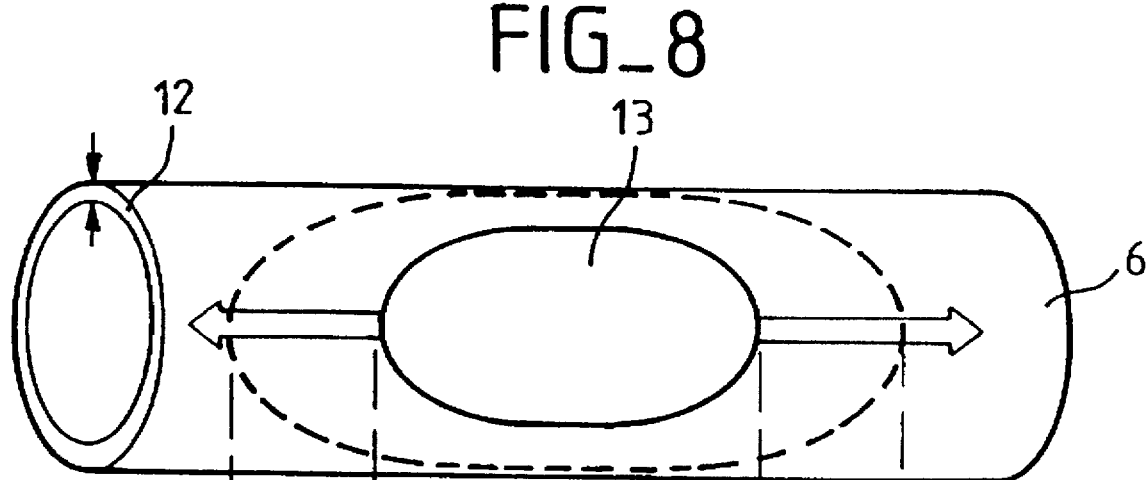
FIG_8
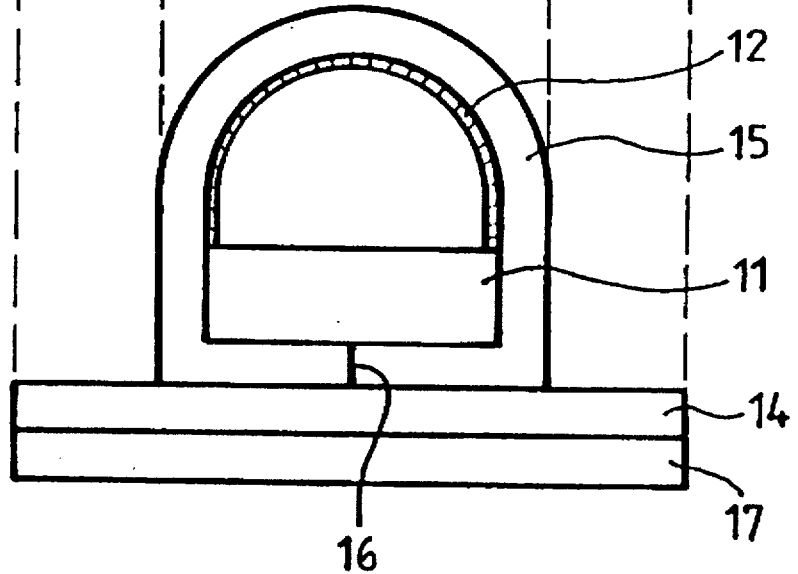
FIG_9

5,695,338

EXPANSION DEVICE FOR ORAL RECONSTRUCTION AND METHOD FOR THE INSTALLATION OF THE EXPANSION DEVICE UNDER A PATIENT'S GUM IN ORDER TO CARRY OUT ORAL RECONSTRUCTION IN CASES OF BONE LOSS

BACKGROUND OF THE INVENTION

The present invention consists of an expansion device based on a silicone film that facilitates oral reconstruction in the event of bone loss and a method for the installation of the expansion device beneath a patient's gum in order to carry out oral reconstruction.

When a tooth is removed, the alveolar bone is gradually resorbed because of the stimulus of loss of ossification-inducing pressure from the teeth. As the resorption process advances, the size of the bone gets reduced, i.e. the bone on which the dental roots are positioned start shrinking (this is the alveolar process).

The absence of just one tooth can set off modifications throughout the dental arch and even prompt a possible softening (loss of insertion) which may cause the loss of other teeth. The absence of several teeth aggravates the problem. Bone loss may finally modify the patient's appearance and, depending on the loss, may make him incapable of receiving brides, implants or even dentures.

It is then necessary to carry out several surgical operations to reconstruct the alveolar ridge of the mandible or maxilla.

Although these methods of surgical reconstruction have been successfully performed, this type of operation has had drawbacks. Certain methods have involved opening the mucoperiosteal tissue along the entire length of the atrophied alveolar ridge and then placing the substance, calcium hydroxyapatite, at the top of the edentulous alveolar ridge and at the same time holding the hydroxyapatite in position while suturing the delicate mucoperisteal tissue, which was stretched, to bring it back to its initial position. This surgical operation has had drawbacks such as the tearing of the mucoperisteal tissue and the shifting of the hydroxyapatite as well as insufficiency in the reconstitution of the alveolar ridge of the mandible or maxilla.

Furthermore, conventional surgical techniques have generally given rise to difficulties in maintaining the hydroxyapatite particles along the alveolar ridge to prevent them from migrating towards the lingual sulci or the buccal and labial vestibules. However, attempts to obtain adequate tissue coverage generally resulted in obliterating the buccal vestibule, necessitating vestibuloplasty. There have also been cases of lip paresthesia caused by damage to the nerves of the chin. The surgical device known as the stent is commonly used to control particles. This could give rise to an erosion of the mucosa and deshiscence of the hydroxyapatite from stent pressure.

Apart from surgery for oral reconstruction known in the prior art, there also exist inflatable or expandable devices placed beneath the periosteum in the edentulous mandibular or maxillary ridge.

These inflatable devices have advantages as compared with the surgical techniques of the prior art inasmuch as they avert necrosis, tearing of tissues, paresthesia of the chin nerve, migrations of hydroxyapatite, the obliteration of the buccal vestibule, the erosion of the mucosa, dehiscence, hematoma formation, etc.

However, these known inflatable devices have one or more cannulae by which the expanding liquid is introduced. Whereas the expansion device proper is placed beneath the subperiosteal tissue, its cannula remains outside the mouth. This is very uncomfortable. Furthermore, the cannula, by virtue of its being a link between the interior of the gum and the exterior, increases the risk of infection.

OBJECT AND SUMMARY OF THE INVENTION

The object of the present invention is to provide an expansion device similar to those known in the prior art but which can be applied to the mouth without any risk or discomfort for the patient. In a document U.S. Pat. No. 4,719,918, an expansion device has already been described with a cannula comprising, as a variant, a plate made of a material forming a natural valve placed flat against a wall of a closed pouch forming a device and designed to receive a filling needle. The valve is even placed preferably inside the pouch. This device furthermore comprises a protection system against its being perforated completely through, to prevent its deterioration during filling. This protection system is formed by a hard flat piece bonded to an opposite face of the pouch with respect to the one bearing the valve.

This embodiment has drawbacks inasmuch as the protective flat piece is thus placed on a bottom of the pouch and reduces its flexibility. High flexibility is however necessary when the pouch is laid on the bone during the operation. The pouch then matches the profile of the bone more easily. Furthermore, the insertion of the filling needle (which is done every three days for example) should not be done except in a precise direction which is the one presented by the alignment of the valve with the protective flat piece. This is sometimes delicate given the position of the pouch in the patient's mouth.

To resolve these problems, in the invention, in a pouch such as this, a protective cover portion is directly hooked to the wall or base bearing the valve piece, in the vicinity of the valve or even preferably on the valve itself and not on the wall of the pouch opposite the wall that bears the valve. This cover portion, which then has a concave shape and no longer a flat shape, provides great tolerance of insertion of the filing needle at the time of the injection since it is closer to this valve. The concave shape of the cover portion contributes to the same technical result providing protection. In the U.S. patent referred to, the tolerance of orientation of the needle at the time of injection is more restricted. Or else, the protective flat piece has to be bigger, thus reducing flexibility. As shall be seen hereinafter, it is not, however, more difficult to make the pouch of the invention. It necessitates more operations, but these operations are simple.

The above aim is achieved by presenting an expansion device for oral reconstruction formed by a closed pouch made of a film provided at one point with an additional thickness and a protective feature against being perforated right through, characterized in that the protective feature comprises, within the pouch, a concave cover portion positioned so as to be facing the additional thickness, bonded directly to each side of the additional thickness but not on its entire periphery.

BRIEF DESCRIPTION OF THE DRAWINGS

In order to enable a better understanding of this invention, a detailed description is given below as well as appended drawings of which:

FIGS. 8 and 9 show the steps of a method for making a preferred pouch according to the invention.

DETAILED DESCRIPTION OF THE PREFERRED EMBODIMENT

Figure 1:
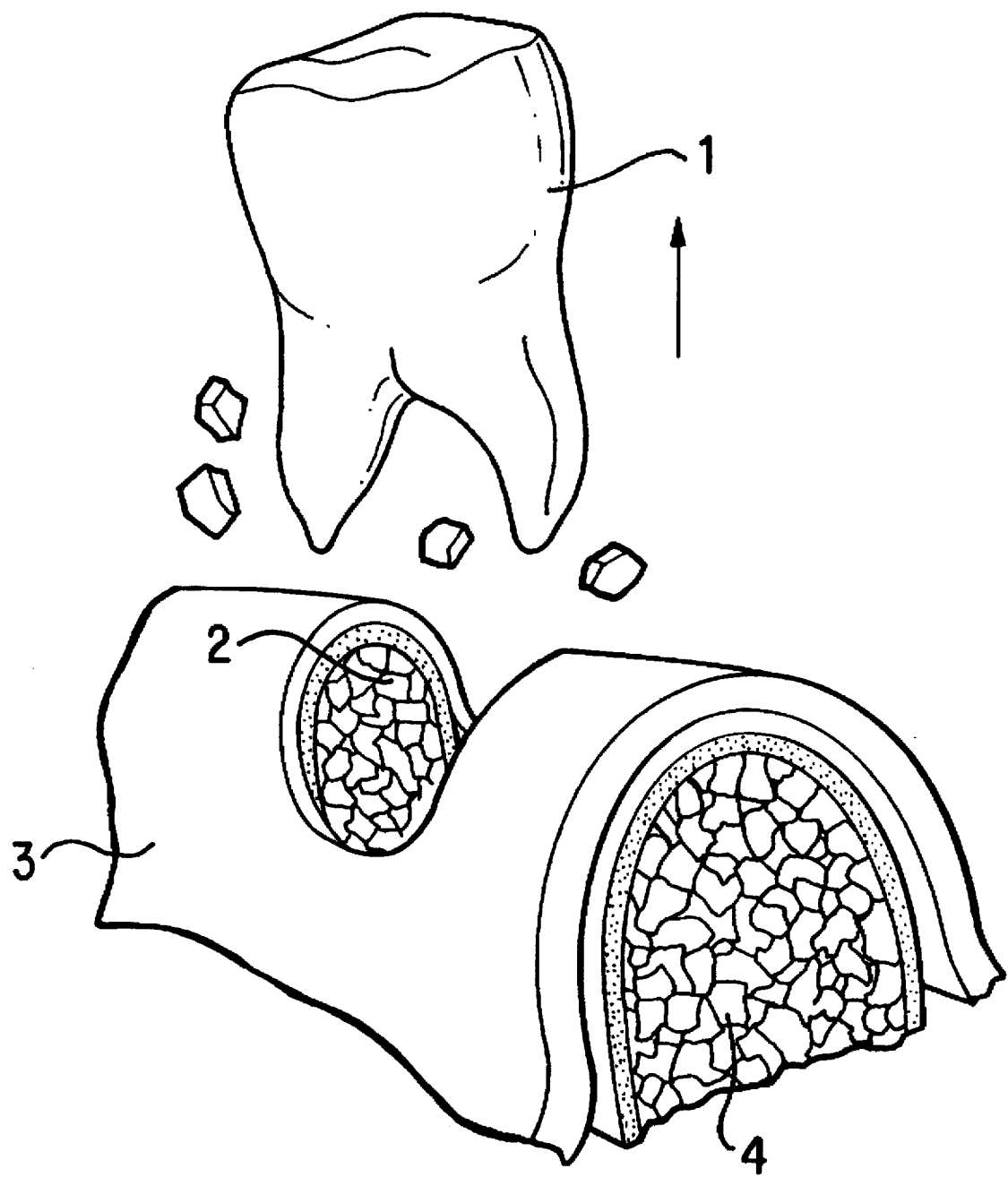
FIG. 1 is a schematic view illustrating the extraction of a tooth.
Figure 2:
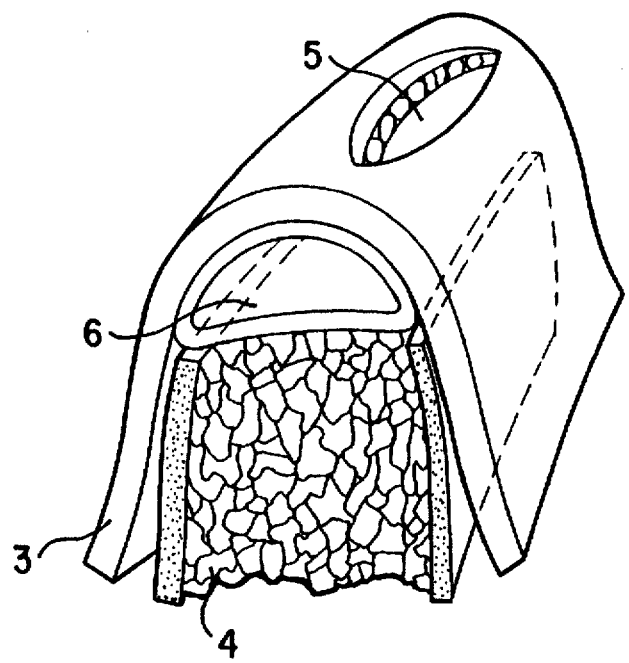
FIG. 2 is a view, also schematic, illustrating the empty expansion device inserted between the bone and the gum.

As mentioned further above, the expansion device or pouch 6 of this invention is made of a silicone film and may have a generally rectangular shape, namely a parallelepiped, or an arc, a half-arc, a small cylinder or even a tooth root, depending on the specific requirements of each case. Namely, the shape, dimensions and curves of the pouch 6 will be those that can be best adapted to the specific case of a patient.

The function of the expansion device 6 is to create an interstice between the gum 3 and eroded bone 4 in order to create a space for the new bone 4'. The expansion device can also be used preventively after an extraction to prevent bone loss if any.

The oral reconstruction method consists in the insertion 5 of the empty expansion device 6 between the gum 3 and the eroded bone 4. The expansion device is then gradually filled with a liquid by means of a syringe 7, care being taken to comply with the expansion capacity of the gum. After a period of four weeks, the expansion device 6 is removed, thus leaving the created new space ready to receive a material 8 that induces bone growth. This material 8 may be lyophilized bone which chemically induces the growth of new bone. Instead of lyophilized bone, it is also possible to use calcium hydroxyapatite which also induces bone growth.

Figure 5:
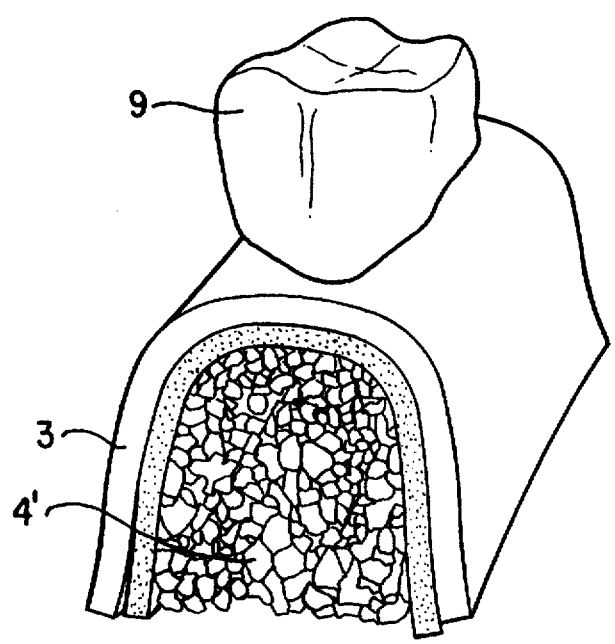
FIG. 5 schematically illustrates the fixing of an implant in the reconstituted alveolar ridge.

Within a maximum period of six months, the alveolar ridge is reconstituted and any patient whomsoever can undergo the installation of implants 9 or prostheses as shown in FIG. 5.

The present invention, described and illustrated herein, can be modified in various ways within the framework of the spirit and scope of the invention defined in the appended claims.

Figure 6:
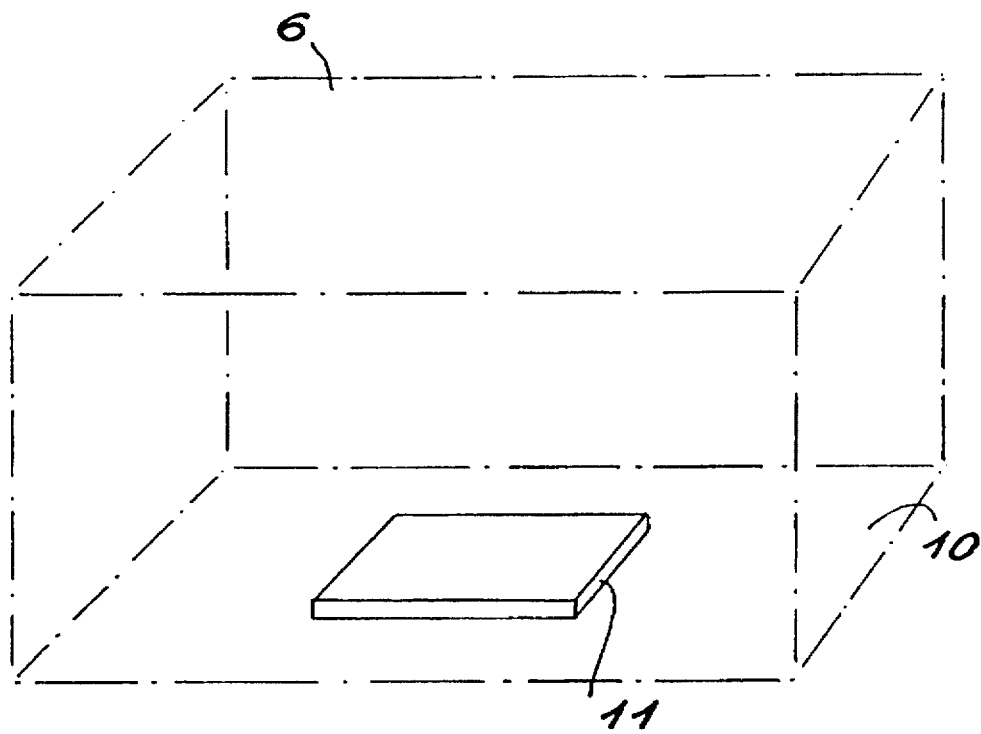
FIGS. 6 and 7 give a schematic view of the essential parts of the invention.

With respect to the known expansion device, the expansion device or pouch 6 of the invention comprises, in the wall that constitutes it, an additional thickness. For example, as can be seen in FIG. 6, on a portion 10 of a film made of silicone or of any other elastic material, designed to form an expansion device 6, a flat piece 11, preferably made of a same material is bonded in an additional thickness. In one example, the thickness of the film is 0.1 mm and that of the flat piece 11 is 1 mm to 1.5 mm. The additional thickness may nevertheless be obtained by other means, for example by the molding of a wall of the pouch to be made in a mold containing a cavity. Then, with this portion 10 of film thus prepared, a pouch is made. For example, various pieces of film are put together to make the shapes indicated: rectangular, arc-shaped, half-arc, cylindrical or even cone-shaped for dental roots. In doing so, it is seen to it that the additional thickness formed by the flat piece occupies, in the shape made, a position from where it will be accessible in the patient's mouth. For example, this position is close to the upper part of the gum. In practice, preferably, the flat piece 11 is positioned so that can no longer be seen when pouch construction is complete: it is fixed to the inside of the pouch.

Figure 3:
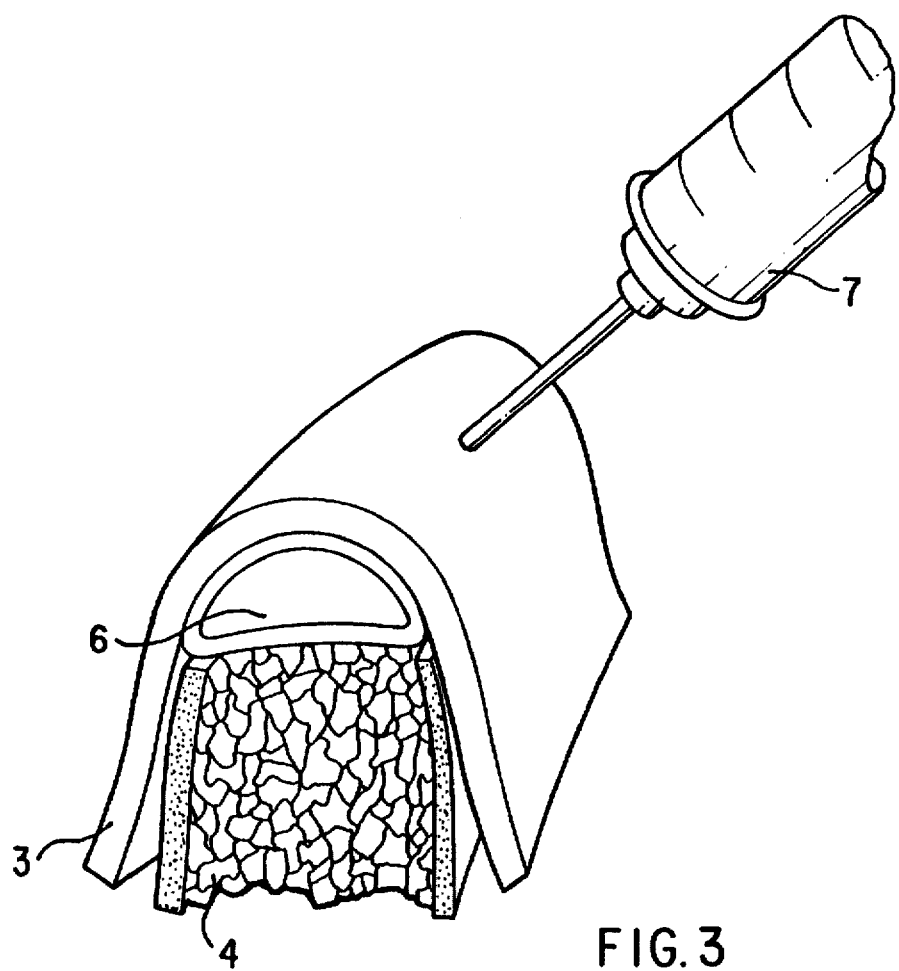
FIG. 3 schematically illustrates the pre-filling of the expansion device with a liquid.
Figure 4:
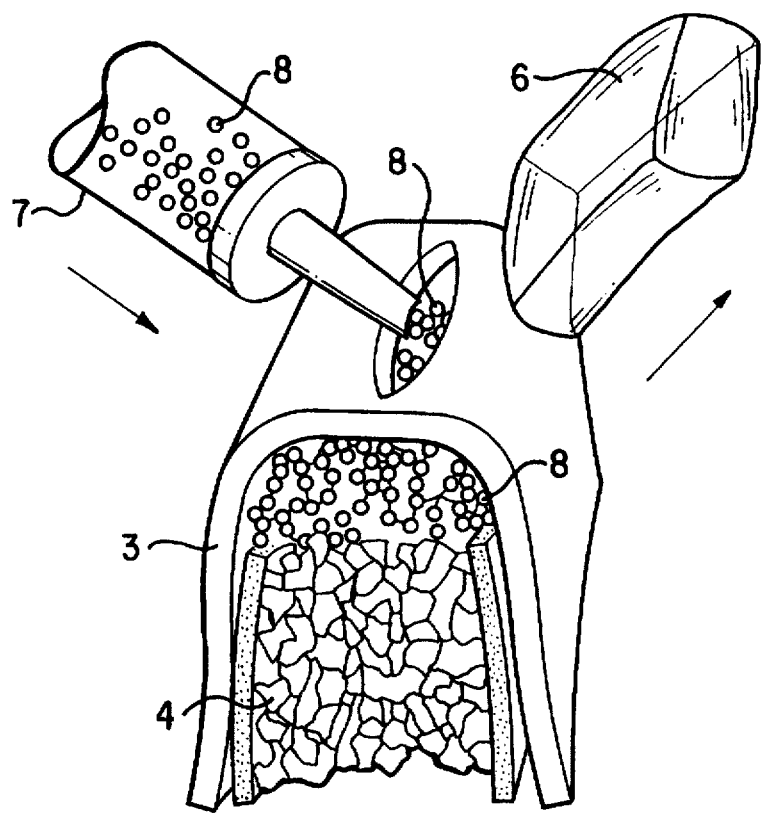
FIG. 4 illustrates the method for the removal of the expansion device and the placing of the lyophilized bone in the vacant space.

For the gradual filling of the expansion device, a syringe (FIG. 3) is brought closer to the pouch 6. The pouch 6 is then pierced at the position of the additional thickness 11 through the gum, and gradually the pouch is filled with a liquid. When the syringe is removed, the material of the flat piece 11 acts as a valve piece which tends, by elasticity, to re-occupy the place of the hole created by the syringe. The thickness of the flat piece is such that it then forms a natural valve. It closes automatically. There is no longer any reason for a cannula connecting the pouch to the exterior. The pouch is alone.

Figure 7:
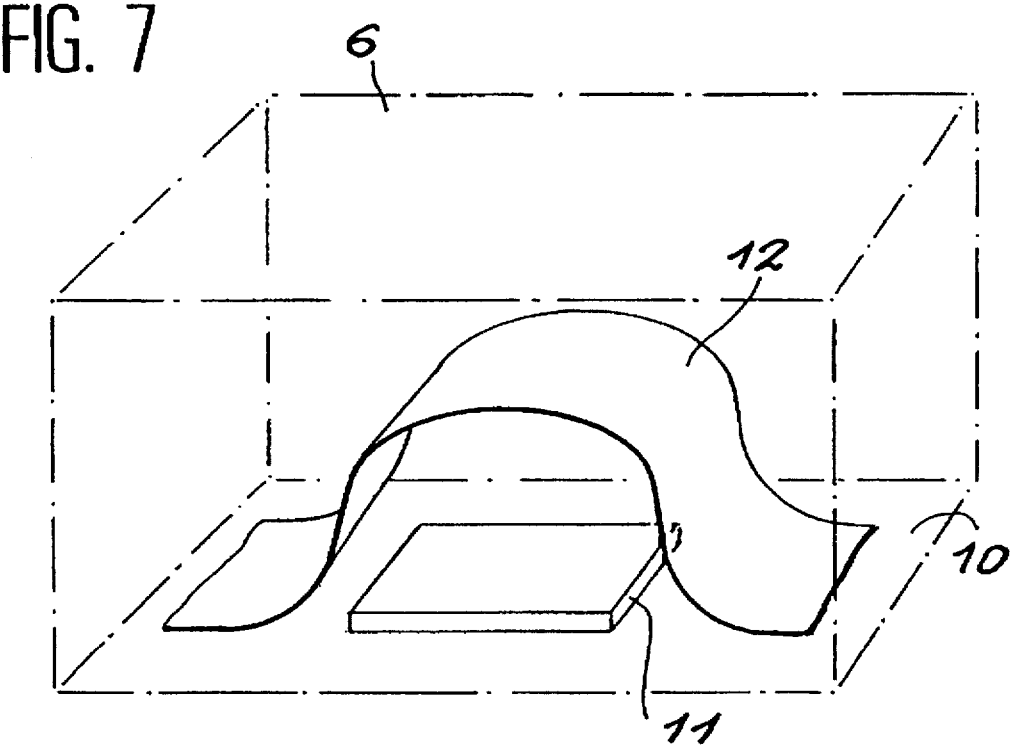

To prevent the pouch 6 from being pierced all the way through when it is being pierced, there is preferably a small protective cover or cover protection 12 placed, FIG. 7, directly above the flat piece 11. The cover portion may be made of metal, for example stainless steel, plastic (for example PVC) or preferably 6.6 type nylon. The cover portion is concave. The cover portion is not a complete half-shell. It has at least side apertures to let through the injected fluid. It is bonded to the film 10 in such a way that, at the end, it is inside the pouch hooked to the flat piece 11. Subsequently, when the pouch is pierced with the syringe 7, the end of the needle of the syringe abuts the cover portion 12 inside the pouch. It becomes impossible to pierce the pouch all the way through. The cover portion 12 preferably is not bonded throughout its periphery. The cover portion 12 is fixed for example by two lugs that preferably directly reach each side of the additional thickness at the same part or base of the wall of the pouch as the one bearing the additional thickness or valve piece. The cover portion, may thus have the shape of a half-shell and be concave so that its concave surface is attached to the base at locations beyond the ends of the flat piece 11. The liquid may therefore flow from inside the pouch through the non-bonded sides of the cover portion.

For conical pouches used for dental roots, such a cover portion may not be necessary because the piercing is done in the direction of the root. There is little risk of piercing the pouch right through. Indeed, in this case, the conical expansion device is pushed in by the tip into the jaw and presents its base provided with the additional thickness.

FIGS. 8 and 9 show a preferred method of making the device according to the invention. The procedure starts with the manufacture of a pouch 6 of the desired shape, a useful part thereof being shown in FIG. 8, for example in the shape of a tube. The pouch 6 is made of a layer 12 of silicone subjected to vulcanization by curing. In this pouch 6, a hole 13 is made having a diameter substantially equal to 4 mm. Then (FIG. 9) there are made a pad 14 of vulcanized silicone with a thickness of 0.2 mm and a diameter of 8 to 10 mm, a flat piece or valve piece 11 made of vulcanized silicone with a thickness of 1 mm and a diameter equal to the diameter of the hole 13 as well as a laterally open, nylon half-shell 12 whose diameter is also equal to that of the hole. The half-shell 12 is then joined to the flat piece 11 by means of an uncured (as yet non-vulcanized) silicone band 15. The bonding takes place naturally, and the band 15 is butt-joined to itself above the pad 14 at 16. The band 15 has a thickness of 0.2 mm. Then, the entire device is fired to obtain, in one assembly, a valve or flat piece 11 hooked to its cover portion 15 and to its base 14 but not yet positioned in the pouch 6. To carry out this positioning, a layer 17 of uncured silicone is attached flat against the underneath of the assembly 11 to 16. Preferably, this layer 17 may be temporally covered with a plastic film that enables handling. The edges of the hole 13 are then moved aside with the fingers and, in the enlarged hole, the assembly is introduced with the cover portion in the front. In practice, at this time, the cover portion temporarily abuts the wall of the pouch 6 opposite the hole. The plastic protective film (if any) is then removed. By pressure and kneading, the edges of the internal face of the pouch 6 are then bonded to the position of the hole against the layer 17. The entire unit is then fired to vulcanize the layer 17 in contact both with the layer 14 and the wall 6. The assembly is then completed.

I claim:

1. An expansion device for oral reconstruction comprising:

an enclosed pouch made of a film, one portion of said pouch forming a base;

a valve piece provided on said base and having an area smaller than an area of said base; and a protective cover which is disposed within said pouch, which is attached directly to said base, and which presents a concave surface which faces said valve piece, said protective cover being dimensioned and configured to prevent said pouch from being pieced all the way through when a needle is inserted into said pouch through said valve piece.

2. Expansion device according to claim 1, wherein said pouch is generally in a shape of a parallelepiped.

3. Expansion device according to claim 1, wherein said pouch is generally in a shape of an arc or a half-arc.

4. Expansion device according to claim 1, wherein said pouch is generally cylindrical in shape.

5. Expansion device according to claim 1, wherein said pouch is generally in a shape of a tooth root.

6. Expansion device according to claim 1, the wherein the valve piece is located inside the pouch.

7. Expansion deice according to claim 6, wherein said protective cover is also attached directly to said valve piece.

8. Expansion device according to claim 7, wherein said protective cover has first and second pairs of opposed end portions, and wherein both end portions of said first pair are attached to said base and to said valve piece and both end portions of said second pair are separated from said base and from said valve piece.

9. An expansion device according to claim 1, wherein the protective cover comprises a vulcanized half-shell mounted on the valve piece and on a pad which is positioned between the valve piece and the base.

10. Expansion device according to claim 9, wherein the pad is fixed by vulcanization to the base.

11. Expansion device according to claim 1, wherein the protective cover is made of nylon.

12. Expansion device according to claim 1, wherein the protective cover is made of plastic.

13. Expansion device according to claim 1, wherein said valve piece comprises a flat piece of film.

14. Expansion device according to claim 1, wherein said concave surface of said protective cover is bonded directly to said base and to said valve piece.

15. An expansion device for oral reconstruction comprising:

an enclosed pouch made of a film, one portion of said pouch forming a base;

a valve piece located within said pouch and supported on said base, said valve piece having an area smaller than an area of said base; and a protective cover which is disposed within said pouch, said protective cover having a concave surface which faces said valve piece, which extends over said valve piece, and which is attached directly to said base at locations disposed beyond opposed ends of said valve piece, said protective cover being dimensioned and configured to prevent said pouch from being pieced all the way through when a needle is inserted into said pouch through said valve piece.

16. Expansion device according to claim 15, wherein said valve piece comprises a flat piece of film.

17. Expansion device according to claim 16, wherein said protective cover has first and second pairs of opposed end portions, and wherein both end portions of said first pair are attached to said base and to said valve piece and both end portions of said second pair are separated from said base and from said valve piece.

18. An expansion device for oral reconstruction comprising:

an enclosed pouch made of a film, one portion of said pouch forming a base;

a valve piece located within said pouch and supported on said base, said valve piece being formed from a piece of flat film and having an area smaller than an area of said base; and a protective cover which is disposed within said pouch, said protective cover having a concave surface which faces said valve piece and which extends over said valve piece, said concave surface of said protective cover being attached directly to said base at locations disposed beyond opposed ends of said valve piece and also being attached directly to said opposed ends of said valve piece, said protective cover being dimensioned and configured to prevent said pouch from being pieced all the way through when a needle is inserted into pouch through said valve piece.

* * * * *